United States Patent [19]

Thomann

[11] Patent Number: 4,481,820

[45] Date of Patent: Nov. 13, 1984

[54] METHOD OF AND AN APPARATUS FOR MEASURING CHARACTERISTIC FEATURES OF FIBROUS MATERIAL

[75] Inventor: Christoph Thomann, Maur, Switzerland

[73] Assignee: Zellweger Uster Ltd., Uster, Switzerland

[21] Appl. No.: 449,616

[22] Filed: Dec. 14, 1982

[30] Foreign Application Priority Data

Jan. 18, 1982 [CH] Switzerland ............................ 269/82
Jan. 18, 1982 [CH] Switzerland ............................ 270/82

[51] Int. Cl.$^3$ ............................................ G01N 29/00
[52] U.S. Cl. ........................................ 73/597; 73/599; 73/160
[58] Field of Search ........................... 73/597, 599, 160

[56] References Cited

U.S. PATENT DOCUMENTS 2,768,524 10/1956 Beard .................................... 73/599
2,966,057 12/1960 Heller .................................... 73/599
3,750,461 8/1973 Felix ...................................... 73/597

FOREIGN PATENT DOCUMENTS 901894 1/1982 U.S.S.R. ................................ 73/597

Primary Examiner—Howard A. Birmiel
Attorney, Agent, or Firm—Antonelli, Terry & Wands

[57] ABSTRACT

The present method relates to the measurement of fibrous material, such as slivers and rovings, by ultrasonics. By a suitable arrangement of a sound source and a sound pick-up with the fibrous material disposed therebetween, only those sound waves arrive at the sound pick-up which have penetrated the fibrous material. All lagging disturbing signals which are generated by reflections and interferences are suppressed by the pulsed operation of the sound source and by the corresponding gating of the sound pick-up, as a result of which, the value to be measured, namely, the quantity of fibers present at any time in the measuring data, is substantially free from disturbing influences. This measured value may be used as a value for the cross-sectional regularity, or as a controlled variable for the production of regular rovings or slivers. The fineness and quantity of the fibrous material which is being considered may be simultaneously determined by the joint evaluation of damping and propagation time delay of the sound waves which are used. This measured value may be used as a value for the fiber fineness, or as a controlled variable for the production of regular fiber mixtures of fiber bales of a different origin.

30 Claims, 8 Drawing Figures

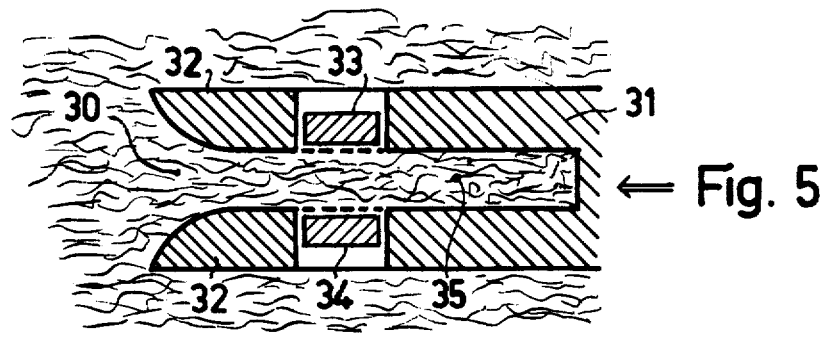
← Fig. 5
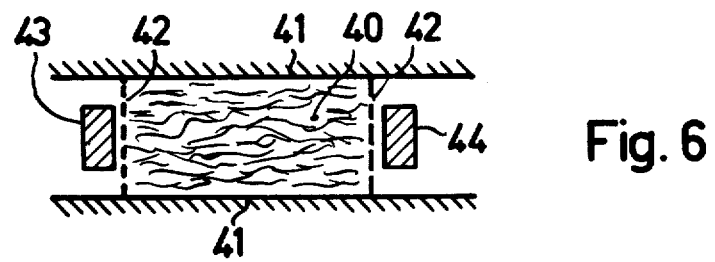
Fig. 6
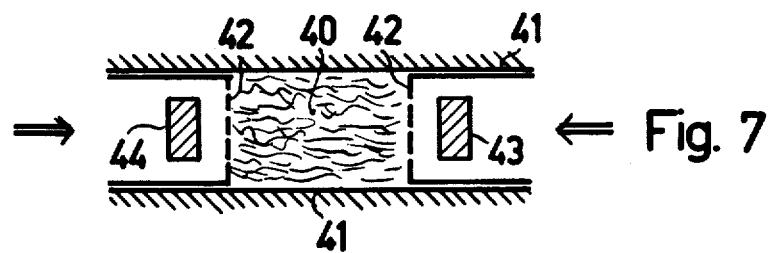
← Fig. 7
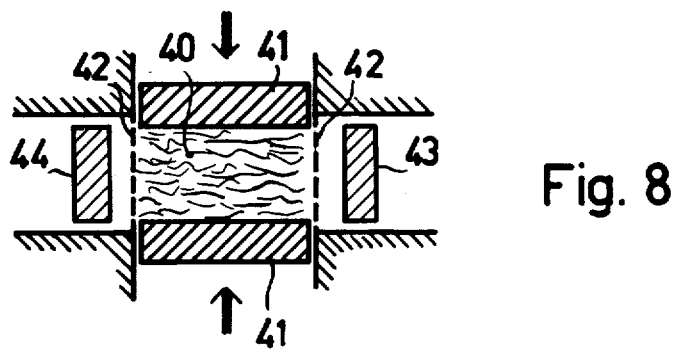
Fig. 8

METHOD OF AND AN APPARATUS FOR MEASURING CHARACTERISTIC FEATURES OF FIBROUS MATERIAL

BACKGROUND OF THE INVENTION

This invention relates to a method of and an apparatus for measuring characteristic features of fibrous material, and it relates in particular to the measurement of the quantity of fibers in textile slivers.

Attempts have been made for a relatively-long time and corresponding methods and apparatus have been developed to determine the quantity of fibers in textile slivers by means of ultrasonics. In this respect, reference is made, for example, to the Heller U.S. Pat. No. 2,966,057, and to the publication by Bobrov, Gorelik and Volosmikov, Teknologia Tekstilnov Promystchlennosti No. 4 (1973), page 115. However, these attempts have been unsuccessful in producing an apparatus of satisfactory accuracy and reliability. An essential reason for this failure lies in the high interference capability of sound waves. In this regard, certain resonances arise in any arrangement which severely disturb the linear or monotonic relationship between fiber quantity and the magnitude of the sound signal.

Another problem which is encountered in determining the quantity of fibers using ultrasonics relates to the fact that even very small openings are sufficient to produce a false or inaccurate measurement, if sound waves are able to pass through these openings from the source to the pick-up without fully penetrating the fibrous material.

BRIEF SUMMARY OF THE INVENTION

The present invention takes these facts into account and relates to a method and an apparatus by which the inherent problems heretofore encountered in the measurement of the characteristic feature of fibrous material are effectively eliminated.

The basic difficulties are overcome by positioning the fibrous material between a sound source (abbreviated to "source") and a sound pick-up (abbreviated to "pick-up"), and the sound waves arriving at the pick-up are evaluated in a manner such that only those sound waves which arrive at the pick-up on a direct path from the source, without additional reflections, and which have penetrated the fibrous material are evaluated.

According to the present invention, the fibrous material, in particular in case of slivers, is guided by lateral boundary surfaces such that all the sound waves are forced to penetrate the sliver in order to arrive at the pick-up from the source. The lateral boundary surfaces are preferably formed by parallel plates, the magnitude of compression being selected such that the fibrous material rests closely against both plates. This measure prevents the formation of lateral openings, through which sound waves may to some extent or even completely by-pass the fibrous material. Openings of this type, even if they are only narrow openings, have an effect similar to a short circuit in electric circuits and thus may severely disrupt measurements.

In practice, a reflection-free sound transmission may, for the most part, only be achieved at a considerable expense, if at all. Therefore, according to the present invention to determine the characteristic features of fibrous material, the source emits intermittent sound waves through the fibrous material to the pick-up. The pick-up then evaluates those sound waves which are first to arrive and suppresses the sound waves which arrive later. Sound waves which undergo additional reflections cover a longer distance from the source to the pick-up, and so they arrive later at the pick-up and are suppressed. The length of the pauses between the emitted sound waves is to be selected such that all resonances which arise may decay again.

The damping and the propagation time delay may both be used to determine the quantity of fibers or other characteristic features, for example, the fineness of the fibrous material, from the sound signal which is evaluated at the pick-up. The propagation time delay also depends on the acoustic frequency which is used. On the other hand, the change in the propagation time as a result of changes in temperature is independent of frequency. Thus, according to the present invention, the temperature dependence may be eliminated by using two or more different frequencies, which results in a substantial improvement in the measurement. The different frequencies may be emitted simultaneously or in an alternating manner by one or more sources. The use of two or more different frequencies may also serve the purpose of determining the distance between the source and pick-up.

According to the present invention, the simultaneous determination of damping and propagation time delay provides the possibility of simultaneously determining two different characteristic features of the fibrous material, for example, the quantity of fibers and the fineness of the individual fibers.

The present invention is distinguished in that it not only allows detection of the damping, but also the propagation time delay which a sound wave undergoes when penetrating a fibrous material. The damping and the propagation time delay both depend on the quantity of fibers being penetrated and on the fineness of the fibers; however, the damping and propagation time delay obey different laws. Thus, based on experimental values and on theoretical calculations, it is possible to simultaneously determine the quantity and the fineness of a sample of fibers from the joint measurement of damping and propagation time delay. This provides the major advantage that the fineness measurement may be carried out on any quantity of fibers.

Another measuring method may also be used which is suitable for determining the quantity of fibers at the same time as determining the fiber fineness from the damping or propagation time delay. Thus, for example, the boundary surfaces may be designed as capacitor plates, with which the quantity of fibers may be determined from the change in capacity through the fibrous material. However, the quantity of fibers may also be determined from the pressure of the fibrous material on the boundary surfaces. It is also possible to determine the quantity of fibers using sound waves which are propagated in the fibrous material itself and not in the air which is between the fibers. These methods are known and thus cannot be a particular object of the present invention. By a joint evaluation of the fineness measurement and the fiber quantity measurement, signals may be obtained, on the one hand for the fineness, which signals are substantially independent of the quantity of fibers, and on the other hand, for the quantity of fibers, which signals are substantially independent of the fineness.

Sound waves in the ultrasonic range may be used according to the present invention. Sound waves of a short wavelength have a more pronounced direction of propagation, and thus, it is even possible to determine the quantity of fibers or the fineness from more extensive fibrous material, such as slivers or fiber bales. In particular, it is also possible to determine the quantity of fibers or the fineness from moving fibrous material.

Moreover, it is insignificant to the present invention whether one or more sources or pick-ups are used. On the other hand, the present invention provides several possibilities for the arrangement of source, pick-up and fibrous material. To measure the fiber fineness, the fiber sample may be introduced into a closed volume, as is the case in the known methods, and a source is positioned on one side and a pick-up is positioned on the other side. An apparatus may also be provided for changing the volume parallel or perpendicularly to the direction of sound, which may be used for optimizing the measurement.

As a result of measuring the fineness where there are very different compressions of the fibrous material, it is also possible to determine the degree of maturity of the fibers.

The source and pick-up may also be positioned in an extensive quantity of fibers.

DESCRIPTION OF THE DRAWINGS

The method and an embodiment of the apparatus will now be described in more detail with reference to the following detailed description of preferred embodiments, and the accompanying drawings, wherein:

FIG. 5 is a sectional view of another measuring apparatus for the measurement in extensive fibrous material;

FIG. 6 is a schematic view of an apparatus for the measurement on a fiber sample;

FIG. 7 is a schematic view of an apparatus for measuring the degree of maturity of fibers; and FIG. 8 is a schematic view of a variant for measuring the degree of maturity of the fibers.

DETAILED DESCRIPTION OF PREFERRED EMBODIMENTS

Figure 1:
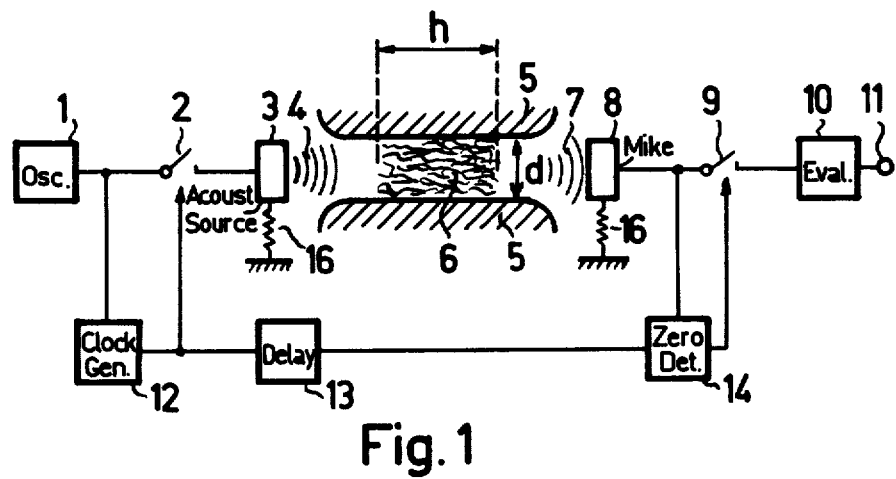
FIG. 1 is a schematic block diagram illustrating an exemplary embodiment of the apparatus according to the present invention.
Figure 2:
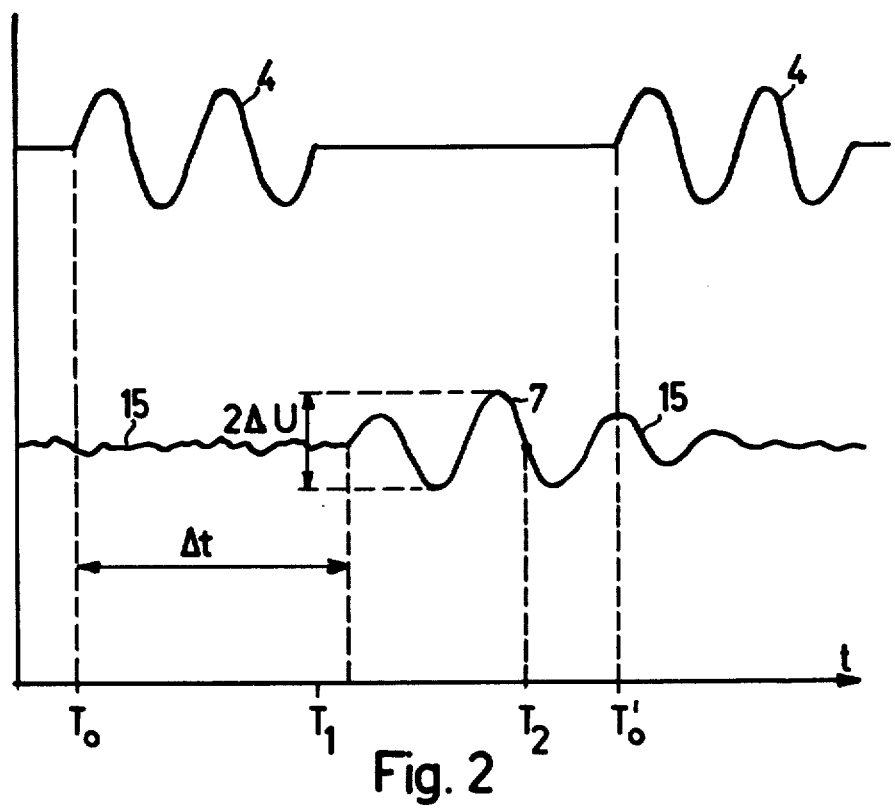
FIG. 2 is a waveform diagram illustrating the time behavior of the source and pick-up.

A source 3 (FIG. 1) periodically emits a sound wave 4 in short bursts, as illustrated in FIG. 2. These sound waves 4 penetrate the fibrous material 6, which is guided by boundary surfaces 5, and they arrive at the pick-up 8. The fibrous material 6 is preferably positioned between the boundary surfaces 5 such that the height h is greater than the spacing d, because considerable nonhomogeneities in the height h may falsify the measurement.

The sound waves 7 emerging from the fibrous material 6 arrive at the pick-up according to FIG. 2 with a time delay $\Delta t$ and an amplitude $\Delta U$. The time delay $\Delta t$ increases proportionally with the quantity of fibrous material which is penetrated, and the amplitude $\Delta U$ decreases exponentially with the quantity of fibrous material penetrated, i.e., :

$$\Delta t = \Delta t_o + \alpha h \zeta \epsilon \quad (1)$$

$$\Delta U = \Delta U_o \cdot e^{-\beta h \zeta \epsilon} \quad (2)$$

In this relation $\alpha$ and $\beta$ represent constants provided by the arrangement, $\zeta$ represents the density of the fibrous material and $\epsilon$ represents the filling factor.

In this arrangement, the pick-up only considers sound waves which arrive in the time between $T_1$ and $T_2$ (see FIG. 2) and suppresses the remainder 15 which would falsify the measurement. As soon as resonances have sufficiently decayed, i.e., at time $T'_o$, the source 3 emits another sound wave 4.

The factors $\alpha$ and $\beta$ depend on the arrangement and on the fineness M of the fibers. The dependence on the fineness M, i.e., $\alpha = \alpha(M)$ and $\beta = \beta(M)$, differs for different values of $\alpha(M)$ and $\beta(M)$. Thus, the quantity of fibers $\mu = h \cdot \zeta \cdot \epsilon$ and the fineness M may be simultaneously determined from the measurement of $\Delta t$ (or $\Delta t - \Delta t_{-o}$) and of $\Delta U$ (or $\Delta U / \Delta U_o$) from equations (1) or (2). Those skilled in the art are familiar with the corresponding calculation process which may be carried out electronically, and thus the details thereof do not need to be described for an understanding of the present invention.

The spacing d between the boundary surfaces 5 may be varied so that the optimum spacing may be adjusted for each quantity of fibers. The source 3, the boundary surfaces 5 and the pick-up 8 may be positioned according to the present invention such that sound waves 7 cannot go around the boundary surfaces 5 without penetrating the fibrous material 6. A possibility of by-passing the fibrous material 6 and the boundary surfaces 5 is only admissible when the detour of the sound wave and the time delay which results therefrom is so great that the corresponding sound wave 7 reaches the pick-up 8 at the moment when the received signals are suppressed.

The source 3 and pick-up 8 must be mounted so that they are acoustically isolated from each other. This arrangement may be achieved, for example, by mounting the source 3 and pick-up 8 on soundproofing damping elements 16, such as buffers. This prevents sound signals from being transmitted by structure-borne noise.

FIG. 1 is a block diagram of a complete measuring arrangement. A sine wave oscillator 1 excites the source 3, which is preferably designed as a piezoelectric element, via an analog switch 2. The sound energy of the source 3 is directed at the pick-up 8, which preferably comprises a microphone. A clock generator 12, which is driven from the oscillator 1, controls the analog switch 2 for the release of the short sound pulses from the piezoelectric element 3 on one side of the path of the fibrous material 6. On the other hand, the output of clock generator 12 is also applied to a time delay element 13, with which the propagation time of the sound through the fibrous material is simulated. After a predetermined time, the output of this time delay element 13 closes another analog switch 9 via a zero crossing detector 14 which also begins counting the zero passages of the output of pick-up 9. The zero crossing detector 14 reopens the analog switch 9 after a predetermined number of zero passages of the received signal and thus again interrupts the transmission of the received signal to an evaluation device 10.

The output pulses of the pick-up 8 are analyzed in the evaluation device 10 with respect to damping and/or propagation time delay and are represented as an output signal 11. The evaluation device 10 may be provided in the form of a computer or corresponding electronic element, such as a microprocessor, which is able to compensate for the temperature from the propagation time delay where there are different frequencies or to determine the distance between the source 3 and the pick-up 8. Furthermore, the evaluation device 10 may be used for simultaneously determining several characteristic features of the fibrous material 6, for example, the quantity of fibers and fiber fineness, by a joint evaluation of the damping and propagation time delay as already described with reference to equations (1) and (2).

The output signal 11 from the evaluation device 10 may be used for various purposes:

(a) representation in an indicator and/or recorder of the cross-sectional regularity of the fibrous material;

(b) as a control or regulating signal to influence cross section determining members on production machines of the textile industry, such as cards and drawing frames;

(c) representation in an indicator and/or recorder of the fiber fineness;

(d) as a control or regulating signal to influence production machines of the textile industry, such as bale removal devices, cards or drawing frames.

However, those skilled in the art are familiar with the design of the necessary electronic circuit to accomplish these purposes, and thus, there is no need to provide a detailed description thereof from an understanding of the present invention.

Finally, the present invention also includes the use of the method for measuring the cross-sectional regularity of slivers, rovings and quantities of sheet-like fibers, and for the control of textile machines based on the measured values of the cross-sectional regularity.

The present invention also includes the use of the method for measuring the fiber fineness to control textile machines based on the measured values of the fiber fineness.

Figure 3:
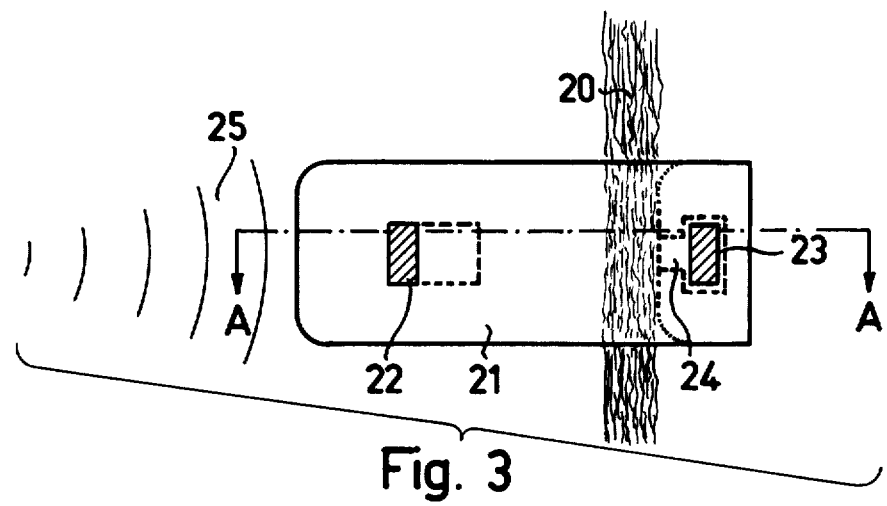
FIG. 3 is a top plan view of the measuring apparatus.
Figure 4:
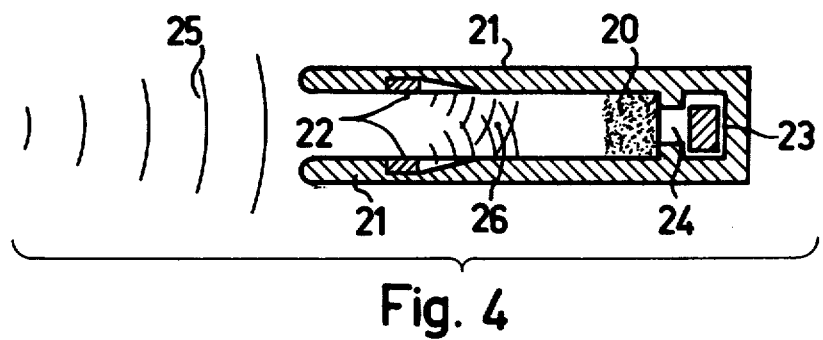
FIG. 4 is a section view of the measuring apparatus taken along line A—A in FIG. 3.

FIGS. 3 and 4 illustrate one embodiment for measuring the regularity/fiber fineness of textile slivers. The sliver 20 is drawn through between two plates 21 which form the boundary surfaces 5 as seen in FIG. 1. The source 22 is located on the open side of the slit which is formed by the two plates 21. One or more sources 22 may be positioned in one or both plates 21. The pick-up 23 is located on the other closed side of the slit. It is screened acoustically and only has one acoustic opening 23 towards the inside of the slit. The sliver 20 is guided over this opening 24. This arrangement makes it possible to damp any foreign and disturbing sound waves 25 from outside to the same extent as sound waves 26 from the source 22. Thus, the measuring member also operates in a disturbance-free manner even where there are very considerable dampings. Moreover, the open slit substantially facilitates handling, because the sliver 20 to be measured may be easily inserted into the slit without having to be separated.

The arrangement of the measuring slit which is formed by the plates 21 may also be effected such that the slit may be sealed on the side opposite the acoustic opening 24 by mechanical means. This measure further prevents the penetration of foreign sound waves 25 into the measuring field and thus into the pick-up 23.

FIG. 5 schematically illustrates an embodiment for measuring the fineness of extensive fibrous material 30. In this embodiment, the measuring member 31 comprises two tongues 32, one tongue containing a source 33 and the other tongue containing a pick-up 34. The measuring member 31 is then introduced into the fibrous material 30 such that the space 35 between the tongues is filled with fibrous material. When there is sufficient fibrous material in the area between the source and the pick-up, the fineness measurement may be carried out. The complete measuring procedure with the introduction of the measuring member into the fibrous material may be automated.

FIG. 6 schematically illustrates an embodiment for measuring the fineness of a fiber sample 40. In this embodiment, the boundary surfaces 41 are formed by, for example, a tube, and the volume in which the fiber sample is located is delimited by acoustically-permeable surfaces 42, which may comprise, for example, perforated plates. These acoustically-permeable surfaces 42 separate the source 43 and the pick-up 44 from the measuring volume containing the fiber sample 40.

In order to optimize the measurement or to determine the degree of maturity, an apparatus may also be provided which changes the measuring volume or the compression of the fibers. In FIG. 7, the volume is changed parallel to the direction of sound, and in FIG. 8 it is changed perpendicularly to the direction of sound.

While I have shown and described several embodiments in accordance with the present invention, it is understood that the same is not limited thereto but is susceptible of numerous changes and modifications as known to a person skilled in the art, and I therefore do not wish to be limited to the details shown and described herein but intend to cover all such changes and modifications as are obvious to one of ordinary skill in the art.

What is claimed is:

1. A method of measuring characteristic features of fibrous material, including measuring the quantity of fibers of textile slivers using sound waves, comprising the steps of directing sound waves which emanate from at least one sound source through the fibrous material so that the sound waves penetrate the fibrous material on their way to at least one sound pick-up, the intensity of the sound waves being damped and the propagation time of the sound waves being delayed according to the quantity of fibers in said fibrous material;

positioning the sound source, fibrous material and sound pick-up such that only the sound waves which penetrate and travel in the fibers of the fibrous material on a direct path arrive at the sound pick-up; and evaluating the output of said sound pick-up to measure the characteristic features of said fibrous material.

2. A method according to claim 1, characterized in that the sound source and the sound pick-up are operated within the ultrasonic range.

3. A method according to claim 1, wherein said positioning step includes restricting the fibrous material by means of lateral boundary surfaces such that the sound waves are forced to penetrate the fibrous material in order to arrive at the sound pick-up from the sound source.

4. A method according to claim 3, wherein the fibrous material is positioned between the boundary surfaces such that all the sound waves which arrive at the sound pick-up through the fibrous material from the sound source penetrate approximately the same quantity of fibers.

5. A method according to claim 1, wherein the sound source emits intermittent sound waves, and wherein said evaluating step comprises evaluating only the sound waves which are received by the sound pick-up a predetermined time after emission of those sound waves by the sound source, so that the sound waves which arrive later are suppressed, whereby interferences and resonances of the sound waves resulting in a different propagation time from those received during said predetermined time are not considered in said evaluation.

6. A method according to claim 1, wherein said positioning step includes positioning the sound pick-up such that any disturbing sound waves not generated by said sound source which might be directed toward said pick-up also have to penetrate the fibrous material in order to arrive at the sound pick-up and consequently they undergo the same damping as the sound waves from the sound source.

7. A method according to claim 1, wherein said evaluating step includes ascertaining the characteristic features of the fibrous material, in particular the quantity or the fineness of the fibers, from the degree of damping of the arriving sound signals at the sound pick-up.

8. A method according to claim 1, wherein said evaluating step includes ascertaining the characteristic features of the fibrous material, in particular the quantity of the fineness of the fibrous material, from the propagation time delay of the sound signals which arrive at the sound pick-up.

9. A method according to claim 8, further including radiating sound waves of a different frequency from the at least one sound source.

10. A method according to claim 9, characterized in that the different propagation time delay is used to compensate for the temperature dependence of the propagation time of the sound wave from the sound source to the sound pick-up where there are different acoustic frequencies.

11. A method according to claim 9, wherein said evaluation step includes simultaneously determining several characteristic features of the fibrous material, including the quantity of fibers, fiber fineness and mixture ratio by a combined evaluation of the damping and propagation time delay of the sound signals which arrive at the sound pick-up.

12. A method according to claim 1, further including subjecting the fibrous material to different compressions, and wherein said evaluation step includes determining the degree of maturity of the fibers from the measurement of the fiber fineness in response to said different compressions of the fibrous material.

13. A method according to claim 1, further including introducing the fibrous material into a closed volume, the boundary surfaces of the volume being designed to be permeable to sound waves on the side of the sound source and on the side of the sound pick-up, prior to directing the sound waves therethrough.

14. A method according to claim 13, further including varying the volume containing the quantity of fibers by moving one or more boundary surfaces.

15. A method according to claim 1, further including introducing the sound source and the sound pick-up into an extensive quantity of fibers such that the space between the sound source and the sound pick-up is filled with fibrous material.

16. A method according to claim 1, further including radiating sound waves of a different frequency from the at least one sound source.

17. The method according to claim 1, wherein the characteristic feature measured is the cross-sectional irregularity of slivers and rovings.

18. The method according to claim 1, wherein the characteristic feature measured is the layer thickness of sheet-like fiber quantities.

19. The method according to claim 1, wherein the result of said evaluating step is used to control textile machines, in particular cards and drawing frames to obtain regular slivers.

20. The method according to claim 1, wherein the result of said evaluating step is used to control textile machines, in particular, bale removal devices, to achieve an optimum fiber mixture.

21. An apparatus for measuring characteristic features of fibrous material, in particular, the quantity of fibers of textile slivers, comprising at least one sound source and at least one sound pick-up disposed in predetermined spaced relationship and between which the fibrous material is to be positioned, the characteristic features of which are to be investigated; boundary surface means for guiding and restricting the fibrous material in the area between said sound source and said sound pick-up so that only the sound waves which penetrate and travel in the fibers of the fibrous material on a direct path arrive at said sound pick-up; and means for evaluating the sound signals generated by said sound pick-up and resulting from the sound waves arriving at said sound pick-up.

22. An apparatus according to claim 21, characterized in that said boundary surface means includes a pair of parallel plates having a predetermined spacing.

23. An apparatus according to claim 22, characterized in that said parallel plates form a slit which is open on at least two sides and having at least one closed side.

24. An apparatus according to claim 23, characterized in that said sound pick-up is located on the closed side of the slit and is screened acoustically except for one acoustic opening directed towards the inside of the slit, said one sound source being located on the opposite side of the slit, and said fibrous material in the form of a sliver being guided through the slit between the sound source and the sound pick-up for measurement of the characteristic features thereof.

25. An apparatus according to claim 24, characterized in that the slit which is formed by said parallel plates is closed on the side opposite the acoustic opening.

26. An apparatus according to claim 23, characterized in that a pair of sound sources are provided one in each plate adjacent the side of said slit opposite said closed end.

27. An apparatus according to claim 23, characterized in that said sound source is provided in one of said plates facing said slit and said sound pick-up is provided in the other plate facing said sound source.

28. An apparatus according to claim 22, further including means for moving at least one of said parallel plates for adjusting the predetermined spacing therebetween.

29. An apparatus according to claim 21, further including means for moving at least one of said sound source and said sound pick-up for adjusting the predetermined spacing therebetween.

30. An apparatus according to claim 21, further including first and second perforated plates disposed adjacent said sound source and said sound pick-up on the side thereof facing the fibrous material, respectively.

* * * * *